United States Patent [19]

Humphrey

[11] 4,409,152

[45] Oct. 11, 1983

[54] CONTINUOUS HIGH PRESSURE PROCESS FOR PREPARING PHENYLPHOSPHONOUS DICHLORIDE

[75] Inventor: Lawrence F. Humphrey, Yonkers, N.Y.

[73] Assignee: Stauffer Chemical Company, Westport, Conn.

[21] Appl. No.: 307,034

[22] Filed: Sep. 30, 1981

[51] Int. Cl.$^3$ .............................................. C07F 9/48
[52] U.S. Cl. .............................................. 260/543 P
[58] Field of Search ................................... 260/543 P

[56] References Cited

U.S. PATENT DOCUMENTS 3,029,282  4/1962  Toy et al. ........................ 260/543
3,864,394  2/1975  Via et al. ........................ 260/543 P

Primary Examiner—Donald B. Moyer
Assistant Examiner—Frederick W. Pepper
Attorney, Agent, or Firm—Hensley M. Flash; William C. Gerstenzang; Howard K. Kothe

[57] ABSTRACT

Phenylphosphonous dichloride is prepared by the continuous reaction of monochlorobenzene, phosphorus trichloride, and elemental phosphorus at elevated pressures and temperatures.

7 Claims, No Drawings

CONTINUOUS HIGH PRESSURE PROCESS FOR PREPARING PHENYLPHOSPHONOUS DICHLORIDE

BACKGROUND OF THE INVENTION

This invention relates to a process for the preparation of phenylphosphonous dichloride. More particularly, the present invention relates to a continuous high-pressure process whereby phenylphosphonous dichloride is produced in high yields with negligible coproduction of polychlorinated biphenyls.

Phenylphosphonous dichloride is an important industrial intermediate which is used in the manufacture of the insecticide EPN, in the manufacture of nylon stabilizers and in the manufacture of organophosphorus compounds.

Of the several known methods by which phenylphosphonous dichloride can be prepared, the "hot tube" process and the batch "autoclave" process are perhaps the two most prominent.

In accordance with the basic hot tube process, benzene and phosphorous trichloride are vaporized to form a mixed vapor stream which is then caused to come into contact with the surface area of a "hot tube". The temperature of the surface of the hot tube is typically maintained at about 600° C. through the use of external electrical heaters.

An improved hot-tube process, wherein monochlorobenzene is added to the reaction mixture, is taught in U.S. Pat. No. 3,029,282.

The batch autoclave process for preparing phenylphosphonous dichloride is described in U.S. Pat. No. 3,864,394, which also teaches that improved yields can be obtained by maintaining a specified relationship between reaction time, reaction temperature and the ratios of phosphorus trichloride and elemental phosphorous to monochlorobenzene present.

Each of these two processes are characterized by certain disadvantages. For example, the hot tube process is subject to formation of tarry residues (about 20-30 grams residue can be formed for every 100 grams phenylphosphonous dichloride produced), which can lead to fouling of downstream equipment, has a tendency to generate undesirable byproducts such as biphenyl, chlorobenzenes and chlorphenyl phosphorous dichloride and is characterized by a very low conversion rate, which makes it necessary to recycle large amounts of unreacted raw materials.

The batch autoclave process, on the other hand, represents a substantial technical advance over the hot tube process, but is still less than satisfactory. The batch process requires a large inventory of reactive materials in the reactor, which can be of concern. In addition, the repeated heating and cooling associated with the batch cycles can have an adverse effect on the life of the reactor.

A process which incorporates the advantages of the batch autoclave process without the disadvantages inherent in the batch nature of the process would represent a welcome advance of the state of the art.

SUMMARY OF THE INVENTION

It has now been found that the advantages of the batch autoclave process can be incorporated into a continuous process.

In accordance with the present invention there is provided a continuous process for preparing phenylphosphonous dichloride having negligible amounts of polychlorinated biphenyls which comprises continuously reacting white or yellow phosphorus with phosphorus trichloride and monochlorobenzene at a temperature ranging from about 275° C. to about 400° C., a pressure ranging from about 40 atm to about 80 atm, and in the presence of a stoichiometric excess of monochlorobenzene.

DETAILED DESCRIPTION OF THE INVENTION

There are many types of reactors which may be used to carry out the reaction of the phosphorus, phosphorus trichloride and monochlorobenzene. The reactors must, of course, be equipped to withstand the relatively high pressures involved. Examples of such reactors are the continuous stirred-tank overflow reactor and the tubular reactor. The tubular reactor can have a greater capacity than that of a continuous-stirred tank overflow reactor, but may be more susceptible to being plugged by residues or unreacted phosphorus. In addition, a tubular reactor can be difficult to control, and heat transfer can be poor because of surface fouling and lack of agitation. For this reason, a continuous stirred-tank overflow reactor is generally preferred.

The capacity of a continuous stirred-tank reactor used in the present process may be estimated to range from about 0.05 to about 0.20 kg. product per liter of reactor volume.

The reactor should be constructed of a corrosion-resistant alloy, such as that sold by the International Nickel Company under the Trademark INCONEL, and should also be equipped with heating means to heat the reactants up to reaction temperatures, as well as to maintain the proper temperature. The reactor should be agitated, although the amount of agitation employed does not seem to be critical.

The feed for the reactor is prepared by mixing the monochlorobenzene and phosphorus trichloride and adding the phosphorus. The mixture should be heated to at least about 60° C. to dissolve the phosphorus. The feed mixture is then preferably fed through a preheater, and heated to about 200° C., prior to being fed to the reactor itself.

The reactor should be maintained at a temperature ranging from about 275° C. to about 400° C., and preferably from about 325° C. to 380° C., and a pressure ranging from about 40 atmospheres to about 80 atmospheres. Nitrogen can be added to the reactor to help maintain the pressure at the desired level, and can also be used in the upstream equipment to create a pressure differential to promote feed flow through the system.

The reaction temperature is an important factor in this process. As reaction temperature is increased, conversion can be increased, but above about 400° C. the amount of byproducts produced, such as polychlorinated biphenyls, can also be increased. At temperatures which are too low on the other hand, conversion can be low.

The product stream taken from the reactor can be distilled to separate the phenylphosphonus dichloride product (as well as diphenyl phosphinous chloride, if desired) from unreacted raw materials, which can then be recycled back to the reactor or feed system. Distillation can also be used to separate the product from any byproduct residues which are formed.

The chemistry of this process can be represented generally by two sequential reaction steps:

1. $3C_6H_5Cl + \frac{1}{4}P_4 \rightarrow C_6H_5PCl_2 + (C_6H_5)_2PCl$

2. $(C_6H_5)_2PCl + PCl_3 \rightleftharpoons 2C_6H_5PCl_2$

And the overall reaction can be represented by the following:

$3C_6H_5Cl + \frac{1}{4}P_4 + PCl_3 \rightarrow 3C_6H_5PCl_2$

The diphenyl phosphinous chloride itself can be a valuable product, and the amount of it which is produced can be increased, within limits, by decreasing the amount of $PCl_3$ present.

In practicing the process of the present invention it is important that a very large excess of monochlorobenzene be used, and this is a radical departure from the batch process. In the batch process, according to U.S. Pat. No. 3,864,394, a minimum of $\frac{2}{3}$ mole phosphorus is required per mole chlorobenzene. These conditions, however, prove inoperable in a continuous process, because unreacted white phosphorus is converted to red phosphorus, which plugs up downstream equipment and also creates a fire hazard. The present process, however, is made operable by using a very large excess of monochlorobenzene, ranging from about 50% to about 100%. When this is done, essentially all of the phosphorus is consumed and the aforementioned difficulties can be substantially curtailed or eliminated.

The conversion achieved and the amount of residues and byproducts formed can vary with a number of factors, such as feed ratios, reaction temperature, residence time and the like. Satisfactory results are generally achieved using the temperature and pressure ranges given above, and residence times ranging from about 1 to about 3 hours. Under these conditions phosphorus conversion to phenylphosphonous dichloride of up to about 80% or more can be realized, while undesirable byproduct formation can be held quite low. Thus, for example, the coproduction of polychlorinated biphenyls can be held to less than about 0.02 grams per 100 gms of phenylphosphonous dichloride.

In order that the present invention be more fully understood, the following example is given by way of illustration. No specific details or enumerations contained therein should be construed as limitations except insofar as they appear in the appended claims. All parts and percentages are by weight unless otherwise specifically designated.

EXAMPLE

A one-liter stainless steel (INCONEL 600) reactor designed for a working pressure of 5000 psi (340 atmospheres) equipped with a subsurface feed line (i.e., a diptube), agitator, bottom valve and heating means was used to conduct several experimental runs. Additional equipment used consisted of a 2 gallon (7.57 liter) carbon steel melt pot equipped with electrical heating tapes to melt and dissolve phosphorus in the phosphorus trichloride/monochlorobenzene solution, a feed tank, a high pressure metering pump, a preheater and a cooler.

Requisite amounts of phosphorus trichloride and monochlorobenzene were weighed-out individually and transferred into the melt tank, which had previously been purged with nitrogen. One-half to one pound (0.2268 kg to 0.4536 kg) of white phosphorus sticks-stored under water-was removed from the original container and weighed under water. The phosphorus sticks were then removed from the water, dipped in acetone to dry, wiped clean with a paper towel and then added to the melt tank.

The contents of the melt tank were then heated under nitrogen pressure to a temperature of at least 60° C. to ensure melting of the phosphorus, and then transferred to the feed tank through a heated line. The feed solution in the feed tank was continuously agitated and maintained at a temperature of from about 65° C. to about 75° C.

The entire system was then pressured to 600–1000 PSIG (43 atm-69 atm) with nitrogen, and the reactor system and transfer lines were heated to the desired temperatures. The feed solution was then introduced to the reactor.

As the feed solution entered the system, the pressure slowly increased due to the compression of nitrogen in the reactor. Since no gaseous by-product was formed, this pressure rise was very slow and continuous venting was not necessary. Periodic venting was effectively substituted; and although this resulted in some system pressure variations during the run, these deviaions were generally confined to a narrow range.

In this manner several test runs were made with the following results.

TABLE I

Yield vs Reactor Conditions

| Run | Feed* | Avg. Feed Rate (g/min.) | Reactor T° C. | P(ATM) | Yield Based on MCB | Yield Based on P4 |
|---|---|---|---|---|---|---|
| 1 | A | 19.7 | 324 | 54.4 | Negligible | |
| 2 | A | 16.8 | 338 | 61.2 | 10 | 12 |
| 3 | A | 6.58 | 365 | 62.9 | 44 | 49 |
| 4 | A | | Feed system plugged | | | |
| 5 | B | 7.2 | 341 | 59.5–68.1 | 39 | 73 |
| 6 | B | 46.0 | 334 | 57.1 | 9.5 | 18 |
| 7 | B | 15.4 | 361 | 61.2 | 11 | 20 |
| 8 | B | 9.62 | 368 | 68.0 | 35 | 72 |
| 9 | C | 4.55 | 359 | 68.1 | 46 | 81 |
| 10 | D | 11.7 | 350 | 69.3 | 16 | 62 |
| 11 | E | 9.7 | 369 | 66.0 | 41 | 81 |
| 12 | F | 4.0 | 380 | 61.9 | 49 | 82 |
| 13 | F | 12.0 | 351 | 43.2 | 27 | 45 |
| 14 | F | 11.4 | 375 | 61.2 | 31 | 52 |

*Feed Compositions were as Follows:
A: 59% PCl$_3$, 35% MCB, 6% P$_4$
B: 60% PCl$_3$, 36% MCB, 3.6% P$_4$
C: 53% PCl$_3$, 43% MCB, 15% P$_4$
D: 41% PCl$_3$, 56% MCB, 3.6% P$_4$
E: 42% PCl$_3$, 53% MCB, 5% P$_4$
F: 38% PCl$_3$, 56% MCB, 6.1% P$_4$ The product from each of several runs was distilled and the distillate as well as the residue was analyzed. The results are shown below.

TABLE II

Product Analysis

| Run | % BPD | DISTILLATE PCB's (PPM) | % Biphenyl | PCB's in Residue (PPM) | Estimated PCB make gm/100gmPPD*** |
|---|---|---|---|---|---|
| 5 | 99.7 | 4 | NIL* | 600 | 0.009 |
| 8 | 98.8 | 2 | NIL* | 7,650** | 0.11 |
| 9 | 99.9 | — | — | 635 | 0.013 |
| 10 | 98.5 | — | — | 1,710 | 0.024 |

*Limit of detection for the test used was 2 ppm.
**This run appears to be anomalous, although the cause was not found.
***Phenylphosphonous Dichloride The results of these test runs demonstrate that the process of the present invention can produce high yields of phenylphonphonous dichloride of high purity on a continuous basis, while producing very low quantities of polychlorinated biphenyls.

I claim:

1. A continuous process for preparing phenylphosphonous dichloride having negligible amounts of polychlorinated biphenyl which comprises continuously reacting white or yellow phosphorous with phosphorus trichloride and monochlorobenzene at a temperature ranging from about 275° C. to about 400° C., a pressure ranging from about 40 atm to about 80 atm and in the presence of a stoichiometric excess of from at least about 50% of monochlorobenzene.

2. The process of claim 1 wherein said reaction is conducted in a continuous stirred-tank overflow reactor.

3. The process of claim 2 wherein said stoichiometric excess of monochlorobenzene is an excess of from about 50% to about 100%.

4. The process of claim 3 wherein said reaction temperature ranges from about 325° C. to about 380° C.

5. The process of claim 4 wherein the average residence time of the reaction mixture in said reactor ranges from about 1 to about 3 hours.

6. The process of claim 5 wherein the amount of polychlorinated biphenyls in said phenylphosphonous dichloride is less than about 0.02 grams per 100 grams of phenylphosphonous dichloride.

7. The process of claim 1 wherein diphenyl phosphinous chloride is also produced.

* * * * *

UNITED STATES PATENT AND TRADEMARK OFFICE
CERTIFICATE OF CORRECTION

PATENT NO. : 4,409,152
DATED      : October 11, 1983
INVENTOR(S) : Lawrence F. Humphrey It is certified that error appears in the above–identified patent and that said Letters Patent are hereby corrected as shown below:

Col. 1, line 23, change "phosphorous" to "phosphorus"

Col. 1, line 37, change "phosphorous" to "phosphorus"

Col. 1, line 46, change "phosphorous" to "phosphorus"

Col. 2, line 63, change "phenylphosphonus" to "phenylphosphonous"

Col. 4, line 23, change "deviaions" to "deviations"

Col. 5, line 11, change "phosphorous" to "phosphorus"

Signed and Sealed this

Third Day of January 1984

[SEAL]

Attest:

GERALD J. MOSSINGHOFF

Attesting Officer    Commissioner of Patents and Trademarks